United States Patent
Rougemont

(10) Patent No.: US 12,031,110 B2
(45) Date of Patent: Jul. 9, 2024

(54) ECONOMICALLY OPTIMIZED LENS CLEANING AND STRIPPING SYSTEM

(71) Applicant: ESSILOR INTERNATIONAL, Charenton-le-pont (FR)

(72) Inventor: Aluysio Rougemont, Rio de Janeiro (BR)

(73) Assignee: Essilor International, Charenton-le-Pont (FR)

(*) Notice: Subject to any disclaimer, the term of this patent is extended or adjusted under 35 U.S.C. 154(b) by 586 days.

(21) Appl. No.: 17/252,862

(22) PCT Filed: Jun. 18, 2019

(86) PCT No.: PCT/EP2019/066039
§ 371 (c)(1),
(2) Date: Dec. 16, 2020

(87) PCT Pub. No.: WO2019/243343
PCT Pub. Date: Dec. 26, 2019

(65) Prior Publication Data
US 2021/0130738 A1    May 6, 2021

(30) Foreign Application Priority Data
Jun. 19, 2018 (EP) .................................... 18305767

(51) Int. Cl.
*C11D 3/00* (2006.01)
*A61L 12/00* (2006.01)
(Continued)

(52) U.S. Cl.
CPC ............ *C11D 3/0078* (2013.01); *A61L 12/00* (2013.01); *A61L 12/06* (2013.01); *C11D 1/662* (2013.01);
(Continued)

(58) Field of Classification Search
CPC ....... C11D 3/0078; C11D 1/662; C11D 3/044; C11D 3/2068; C11D 11/0064; C11D 11/007; A61L 12/00; A61L 12/06
See application file for complete search history.

(56) References Cited

U.S. PATENT DOCUMENTS 3,050,422 A * 8/1962 Zak ..................... C11D 7/06
134/40
4,504,405 A * 3/1985 Howes ................ C11D 3/3707
134/42
(Continued)

FOREIGN PATENT DOCUMENTS

CN    101148635    3/2008
CN    101234386    8/2008
(Continued)

OTHER PUBLICATIONS

Machine Translation of CN101148635A (Year: 2008).*
(Continued)

*Primary Examiner* — Sharidan Carrillo
(74) *Attorney, Agent, or Firm* — Norton Rose Fulbright US LLP

(57) ABSTRACT

Systems and methods for cleaning a hard-coated ophthalmic lens and stripping the hard-coating of the hard coated ophthalmic lens in a single pass process are disclosed. The hard-coated ophthalmic lens is sequentially treated with a cleaning solution, an alkaline solution, and a stripping solution. Ultrasonic power is applied to the solutions and the ophthalmic lens during the process. The resulted ophthalmic lens has substantially no sign of chemical attack or residual hard coating or varnishes thereon.

13 Claims, 1 Drawing Sheet

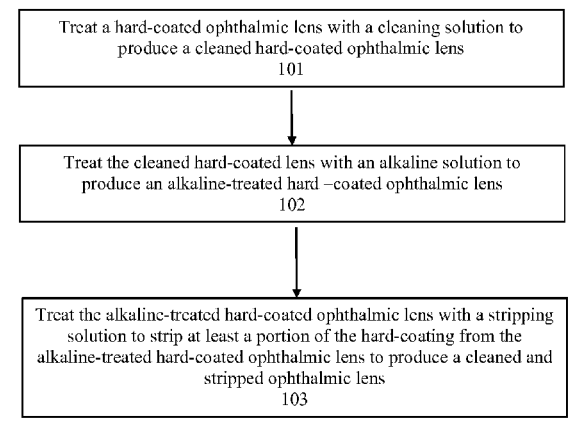

(51) Int. Cl.
*A61L 12/06* (2006.01)
*C11D 1/66* (2006.01)
*C11D 3/04* (2006.01)
*C11D 3/20* (2006.01)

(52) U.S. Cl.
CPC ............ C11D 3/044 (2013.01); C11D 3/2068 (2013.01); *C11D 2111/44* (2024.01); *C11D 2111/46* (2024.01)

(56) References Cited

U.S. PATENT DOCUMENTS

| | | | |
|---|---|---|---|
| 4,734,222 A | | 3/1988 | Winterton et al. |
| 4,780,152 A | * | 10/1988 | Itagaki ............... C11D 17/0073 |
| | | | 134/42 |
| 6,179,931 B1 | * | 1/2001 | Kobayashi ............... G02B 1/10 |
| | | | 134/42 |
| 2006/0079437 A1 | | 4/2006 | Kondo et al. |
| 2013/0309336 A1 | * | 11/2013 | Auberger ............... A01N 37/36 |
| | | | 424/747 |

FOREIGN PATENT DOCUMENTS

| | | | | |
|---|---|---|---|---|
| EP | 0922501 | | 6/1999 | |
| EP | 0958836 A2 | * | 11/1999 | ............... A61L 2/00 |
| KR | 20080023655 | | 9/2008 | |
| WO | WO-9207056 A1 | * | 4/1992 | ............ A61L 12/08 |
| WO | WO-2005115487 A1 | * | 12/2005 | ............ A01N 33/08 |
| WO | WO-2014091575 A1 | * | 6/2014 | ............ A01N 25/02 |

OTHER PUBLICATIONS

Office Action issued in Corresponding Chinese Application No. 201980038257.7, dated May 31, 2021 (English Translation provided).

International Search Report and Written Opinion issued in corresponding International Application No. PCT/EP2019/066039 dated Aug. 9, 2019.

* cited by examiner

100

```
┌─────────────────────────────────────────────────────────────┐
│  Treat a hard-coated ophthalmic lens with a cleaning        │
│  solution to produce a cleaned hard-coated ophthalmic lens  │
│                           101                                │
└─────────────────────────────────────────────────────────────┘
                               │
                               ▼
┌─────────────────────────────────────────────────────────────┐
│  Treat the cleaned hard-coated lens with an alkaline         │
│  solution to produce an alkaline-treated hard-coated         │
│  ophthalmic lens                                             │
│                           102                                │
└─────────────────────────────────────────────────────────────┘
                               │
                               ▼
┌─────────────────────────────────────────────────────────────┐
│  Treat the alkaline-treated hard-coated ophthalmic lens     │
│  with a stripping solution to strip at least a portion of   │
│  the hard-coating from the alkaline-treated hard-coated     │
│  ophthalmic lens to produce a cleaned and stripped          │
│  ophthalmic lens                                             │
│                           103                                │
└─────────────────────────────────────────────────────────────┘
```

ECONOMICALLY OPTIMIZED LENS CLEANING AND STRIPPING SYSTEM

CROSS-REFERENCE TO RELATED APPLICATIONS

This application is a national phase application under 35 U.S.C. § 371 of International Application No. PCT/EP2019/066039 filed Jun. 18, 2019 which claims priority to EP Application No. 18305767.8 filed Jun. 19, 2018, the entire contents of each disclosure is specifically incorporated by reference herein without disclaimer.

FIELD OF THE INVENTION

The present invention generally relates to systems and methods for cleaning optical lenses. More specifically, the present invention relates to methods and systems for cleaning a hard coated optical lens and stripping a hard coating of the hard-coated optical lens in a single pass process.

BACKGROUND

A cleaning and stripping process is used to remove particles and chemical products from optical lenses after the surfacing and polishing steps. At the same time, the cleaning and stripping process is capable of stripping manufacturing varnishes before any new coatings can be applied to the lenses. Furthermore, the cleaning and stripping process can be used to remove a failed or defected hard coating on a lens before another hard coating can be applied thereon. In general, this cleaning and stripping process is imperative to the quality of the final lens products.

Conventionally, a standard method used to clean hard-coated lenses and strip the hard coatings or manufacture varnishes from the hard-coated lenses requires nine different chemical products, including seven of them purchased from specific suppliers, a sodium hydroxide solution, and a detergent from common suppliers. This can cause difficulties in logistics, as many of the chemical products have to be imported from different countries and the importation process from these countries can be complicated. Furthermore, this method also requires cooperation between two separate cleaning apparatuses. Thus, the initial capital expenditure for using this method can be relatively high. Moreover, the standard method consumes a large amount of chemicals and generates toxic chemical wastes, resulting in high environmental impact. Furthermore, the whole process takes more than one hour to complete and is carried out with intensive water and electricity consumption. Therefore, the total operating cost for this standard method is high.

Overall, while methods of cleaning and stripping hard coatings from hard coated lenses exist, the need for improvements in this field persists in light of at least the aforementioned drawbacks of the conventional methods.

BRIEF SUMMARY OF THE INVENTION

A solution to at least some of the above-mentioned problems associated with methods for cleaning and stripping a hard coating from a hard-coated optical lens has been discovered. The solution resides in a single-pass process for cleaning a hard-coated lens and stripping at least a portion of the hard coating. Notably, the process requires only one of the cleaning apparatuses used in a conventional cleaning and/or stripping process, thereby reducing the initial capital expenditure. Additionally, this process uses low cost, low toxicity, and easily accessible chemicals, resulting in reduced operating and/or logistic costs and lowered environmental impact. This process further reduces about 50% of the operating time, electricity, and water consumption compared to conventional methods. Thus, it is capable of reducing overall costs for cleaning and stripping hard coatings from optical lenses. In general, the process of the present invention provides a technical advantage over at least some of the problems associated with the currently available methods for cleaning and stripping hard coatings from optical lenses mentioned above.

Some embodiments of the present invention are directed to a single-pass process for cleaning a hard-coated ophthalmic lens and stripping at least a portion of the ophthalmic lens hard-coat. The process may comprise treating the hard-coated ophthalmic lens with a cleaning solution to produce a cleaned hard-coated ophthalmic lens. The process may comprise treating the cleaned hard-coated ophthalmic lens with an alkaline solution to produce an alkaline-treated hard-coated ophthalmic lens. The process may comprise treating the alkaline-treated hard-coated ophthalmic lens with a stripping solution to strip at least a portion of the hard-coat from the alkaline-treated hard-coated ophthalmic lens to produce a cleaned and stripped ophthalmic lens.

In some aspects, each of the treating steps may be independently performed at a temperature that is at least 10° C. greater than ambient temperature. In some instances, the cleaning solution may comprise 10 wt. % to 40 wt. % of an organic solvent and all ranges and values there between including 10 to 12 wt. %, 12 to 14 wt. %, 14 to 16 wt. %, 16 to 18 wt. %, 18 to 20 wt. %, 20 to 22 wt. %, 22 to 24 wt. %, 24 to 26 wt. %, 26 to 28 wt. %, 28 to 30 wt. %, 30 to 32 wt. %, 32 to 34 wt. %, 34 to 36 wt. %, 36 to 38 wt. %, and 38 to 40 wt. %. The cleaning solution may comprise 1 wt. % to 20 wt. % of an alkaline component and all ranges and values there between including ranges of 1 to 2 wt. %, 2 to 4 wt. %, 4 to 6 wt. %, 6 to 8 wt. %, 8 to 10 wt. %, 10 to 12 wt. %, 12 to 14 wt. %, 14 to 16 wt. %, 16 to 18 wt. %, and 18 to 20 wt. %. The cleaning solution may comprise 0.5 wt. % to 10 wt. % of a surfactant and all ranges and values there between including ranges of 0.5 to 1.0 wt. %, 1.0 to 1.5 wt. %, 1.5 to 2.0 wt. %, 2.0 to 2.5 wt. %, 2.5 to 3.0 wt. %, 3.0 to 3.5 wt. %, 3.5 to 4.0 wt. %, 4.0 to 4.5 wt. %, 4.5 to 5.0 wt. %, 5.0 to 5.5 wt. %, 5.5 to 6.0 wt. %, 6.0 to 6.5 wt. %, 6.5 to 7.0 wt. %, 7.0 to 7.5 wt. %, 7.5 to 8.0 wt. %, 8.0 to 8.5 wt. %, 8.5 to 9.0 wt. %, 9.0 to 9.5 wt. %, 9.5 to 10.0 wt. %. The cleaning solution may comprise a balance of water. In some instances, the stripping solution may comprise 10 wt. % to 40 wt. % of an organic solvent and all ranges and values there between including ranges of 10 to 12 wt. %, 12 to 14 wt. %, 14 to 16 wt. %, 16 to 18 wt. %, 18 to 20 wt. %, 20 to 22 wt. %, 22 to 24 wt. %, 24 to 26 wt. %, 26 to 28 wt. %, 28 to 30 wt. %, 30 to 32 wt. %, 32 to 34 wt. %, 34 to 36 wt. %, 36 to 38 wt. %, and 38 to 40 wt. %. The stripping solution may comprise 1 wt. % to 20 wt. % of an alkaline component and all ranges and values there between including ranges of 1 to 2 wt. %, 2 to 4 wt. %, 4 to 6 wt. %, 6 to 8 wt. %, 8 to 10 wt. %, 10 to 12 wt. %, 12 to 14 wt. %, 14 to 16 wt. %, 16 to 18 wt. %, and 18 to 20 wt. %. The stripping solution may comprise 0.5 wt. % to 10 wt. % of a surfactant and all ranges and values there between including ranges of 0.5 to 1.0 wt. %, 1.0 to 1.5 wt. %, 1.5 to 2.0 wt. %, 2.0 to 2.5 wt. %, 2.5 to 3.0 wt. %, 3.0 to 3.5 wt. %, 3.5 to 4.0 wt. %, 4.0 to 4.5 wt. %, 4.5 to 5.0 wt. %, 5.0 to 5.5 wt. %, 5.5 to 6.0 wt. %, 6.0 to 6.5 wt. %, 6.5 to 7.0 wt. %, 7.0 to 7.5 wt. %, 7.5 to 8.0 wt. %, 8.0 to 8.5 wt. %, 8.5 to 9.0 wt. %, 9.0 to 9.5 wt. %, 9.5 to 10.0 wt. %. The stripping solution may comprise a balance of water. In some aspects, the organic solvent may be an alkyl glycol solvent. Non-limiting examples of the alkyl glycol solvent may include butyldiglycol or dipropylene glycol. In some aspects, the surfactant may include a monosaccharide. Non-limiting example of the monosaccharide may include D-glucopyranose. In some aspects, the alkaline component may include sodium hydroxide and/or potassium hydroxide.

In some embodiments, the ophthalmic lens may be rinsed with water after each of the treating steps. In some aspects, the steps of rinsing the ophthalmic lens with water may be performed at ambient temperature. The water used for each of the rinsing steps may be independently selected from soft water, demineralized water, and deionized water. In some embodiments, ultrasonic power may be transmitted to the ophthalmic lens during at least one of the treating steps. Additionally or alternatively, ultrasonic power may be transmitted to the ophthalmic lens during at least one of the water rinsing steps.

Some embodiments of the invention are directed to a single-pass cleaning and stripping system for cleaning a hard-coated ophthalmic lens and stripping at least a portion of the ophthalmic lens hard-coat. The system may comprise a single apparatus adapted to clean the ophthalmic lens with a cleaning solution. The cleaning solution may comprise 10 wt. % to 40 wt. % of an organic solvent, 1 wt. % to 20 wt. % of an alkaline component, 0.5 wt. % to 10 wt. % of a surfactant; and a balance of water. The single apparatus may be adapted to strip at least a portion of the hard-coat from the hard-coated ophthalmic lens with a stripping solution. The stripping solution may comprise 10 wt. % to 40 wt. % of an organic solvent, 1 wt. % to 20 wt. % of an alkaline component, 0.5 wt. % to 10 wt. % of a surfactant, and a balance of water.

The following includes definitions of various terms and phrases used throughout this specification.

A "polymerized lens comprising at least one polymer" can include a thermally-polymerizable composition, a photo-polymerizable composition, or a mixture thereof. A thermally-polymerizable composition is a composition where polymerization occurs upon exposure to an elevated temperature. A photo-polymerizable composition is a composition where polymerization occurs upon exposure to actinic radiation including, but not limited to, UV, visible, IR, microwave, etc. As used herein polymerizing or polymerization refer to a chemical reaction that results in bonding of one or more monomers or oligomers to each other to form a polymer.

Any embodiment of any of the disclosed compositions and/or methods can consist of or consist essentially of— rather than comprise/include/contain/have—any of the described elements and/or features and/or steps. Thus, in any of the claims, the term "consisting of" or "consisting essentially of" can be substituted for any of the open-ended linking verbs recited above, in order to change the scope of a given claim from what it would otherwise be using the open-ended linking verb.

The term "substantially" and its variations are defined as being largely but not necessarily wholly what is specified as understood by one of ordinary skill in the art, and in one non-limiting embodiment substantially refers to ranges within 10%, within 5%, within 1%, or within 0.5%.

The term "about" or "approximately" or "substantially unchanged" are defined as being close to as understood by one of ordinary skill in the art, and in one non-limiting embodiment the terms are defined to be within 10%, preferably within 5%, more preferably within 1%, and most preferably within 0.5%. The use of the word "a" or "an" when used in conjunction with the term "comprising" in the claims and/or the specification may mean "one," but it is also consistent with the meaning of "one or more," "at least one," and "one or more than one." As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The terms "inhibiting" or "reducing" or "preventing" or "avoiding" or any variation of these terms, when used in the claims and/or the specification, include any measurable decrease or complete inhibition to achieve a desired result.

The term "effective," as that term is used in the specification and/or claims, means adequate to accomplish a desired, expected, or intended result.

The use of the words "a" or "an" when used in conjunction with the term "comprising," "including," "containing," or "having" in the claims or the specification may mean "one," but it is also consistent with the meaning of "one or more," "at least one," and "one or more than one."

The term "primarily," as that term is used in the specification and/or claims, means greater than any of 50 wt. %, 50 mol. %, and 50 vol. %. For example, "primarily" may include 50.1 wt. % to 100 wt. % and all values and ranges there between, 50.1 mol. % to 100 mol. % and all values and ranges there between, or 50.1 vol. % to 100 vol. % and all values and ranges there between.

The compositions and methods for their use can "comprise," "consist essentially of," or "consist of" any of the ingredients or steps disclosed throughout the specification.

Other objects, features and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

BRIEF DESCRIPTION OF THE DRAWINGS

For a more complete understanding, reference is now made to the following descriptions taken in conjunction with the accompanying drawings, in which:

FIG. 1 shows a schematic flowchart for a process of cleaning a hard-coated ophthalmic lens and stripping hard-coating of the ophthalmic lens, according to embodiments of the invention.

DETAILED DESCRIPTION

Conventionally, hard coatings and/or manufacturing varnishes are stripped from optical lenses via cooperation between two apparatuses using nine different chemical products and/or solutions. There are fourteen total steps in the conventional method and it takes more than one hour to complete stripping hard-coatings form lenses with intensive electricity and water consumption, resulting in high operating cost. Furthermore, conventional methods have high environmental impact due to the large amount of toxic chemicals it consumes and generates. The present invention provides a solution to at least some of the problems. The solution is premised on a single-pass process for cleaning a hard-coated ophthalmic lens and stripping at least a portion of the ophthalmic lens hard-coating. The process of the present invention includes using five low cost, easily accessible, and low toxicity chemicals to improve the economic feasibility and environmental impact for cleaning and stripping hard coatings from lenses. The process of the present invention is directed to a single-pass process using a single apparatus with a reduced processing time. Therefore, the method of the present invention is capable of reducing the capital expenditure, energy, and water consumption for cleaning and stripping hard-coated lenses.

These and other aspects of the present invention are explained more fully with reference to the non-limiting embodiments that are illustrated in the accompanying drawing and detailed in the following description. It should be understood, however, that the detailed description and the specific examples, while indicating embodiments, are given by way of illustration only, and not by way of limitation. Various substitutions, modifications, additions, and/or rearrangements will be apparent to those of ordinary skill in the art from this disclosure.

In the following description, numerous specific details are provided to provide a thorough understanding of the disclosed embodiments. One of ordinary skill in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

As shown in FIG. 1, embodiments of the present invention include method 100 of cleaning a hard-coated ophthalmic lens and stripping at least a portion of the ophthalmic lens hard coating. In embodiments of the invention, the hard coating of the ophthalmic lens comprises prime lacquer (i.e. flexible layer), hard lacquer (i.e. anti-scratch layer), mineral materials layers (i.e. anti-reflection layers), organic layer (i.e. anti-smudge layer), or combinations thereof. In some aspects, non-limiting examples of lacquer include prime varnish with a refractive index (RI)=1.6 comprising (3-(2-Methoxyethoxy) propyl-methyl-bis(trimethylsilyloxy)silane, hard coating varnish with RI=1.6 comprising [3-(2,3-epoxypropoxy)-propyl]-trimethoxysilane, prime varnish with RI=1.5 comprising 2-pyrrolidone-4carboxylic substituted polysiloxanes; hard coating varnish with RI=1.5 comprising (dimethyldiethoxysilane, (3-glycidyloxypropil) trimethoxysilane), and combinations thereof. In embodiments of the invention, the ophthalmic lens may comprise substantially any materials suitable for making an optical lens. Non-limiting examples of materials for making ophthalmic lens may include acrylic, Diethylene glycol bis (allyl carbonate) (e.g., Columbia Resin 39), Cyclic Olefin Polymer (COP), Cyclic Olefin Copolymer (COC), Poly diphenyl carbonate (Polycarbonate), Poly vinildene chloride, Poly dichlorostyrene, Polystyrene sulfide, Polythiourethane, Episulphides based polymer, and combinations thereof.

According to embodiments of the invention, as shown in block 101, method 100 comprises treating the hard-coated ophthalmic lens with a cleaning solution to produce a cleaned hard-coated ophthalmic lens. In some aspects, the treating at block 101 comprises submerging the hard-coated ophthalmic lens and/or non-coated lens in the cleaning solution. The treating at block 101 may further include applying ultrasonic power to the cleaning solution and the hard coated ophthalmic lens. In some aspects of the embodiments, the ultrasonic power at block 101 may have a frequency of about 33 MHz at full scale. In some instances, the ultrasonic power at block 101 may have a frequency of about 25% to 45% of the 33 MHz full scale frequency. The treating at block 101 may include adjusting temperature of the cleaning solution. In some aspects, the temperature at block 101 may be adjusted to at least 10° C. above ambient temperature. In some embodiments, the temperature at block 101 is at about 38° C. In some aspects, the duration of the treating at block 101 may be in a range of 1 to 8 minutes and all ranges and values there between including ranges of 1 to 2 minutes, 2 to 3 minutes, 3 to 4 minutes, 4 to 5 minutes, 5 to 6 minutes, 6 to 7 minutes, and 7 to 8 minutes.

In some aspects, the cleaning solution may comprise an organic solvent, an alkaline component, a surfactant, and a balance of water. The cleaning solution can be nonflammable. According to embodiments of the invention, the cleaning solution comprises 10 to 40 wt. % of the organic solvent and all ranges and values there between including ranges of 10 to 12 wt. %, 12 to 14 wt. %, 14 to 16 wt. %, 16 to 18 wt. %, 18 to 20 wt. %, 20 to 22 wt. %, 22 to 24 wt. %, 24 to 26 wt. %, 26 to 28 wt. %, 28 to 30 wt. %, 30 to 32 wt. %, 32 to 34 wt. %, 34 to 36 wt. %, 36 to 38 wt. %, and 38 to 40 wt. %. The cleaning solution may comprise 1 to 20 wt. % of the alkaline component and all ranges and values there between including ranges of 1 to 2 wt. %, 2 to 4 wt. %, 4 to 6 wt. %, 6 to 8 wt. %, 8 to 10 wt. %, 10 to 12 wt. %, 12 to 14 wt. %, 14 to 16 wt. %, 16 to 18 wt. %, and 18 to 20 wt. %. The cleaning solution may comprise 0.5 to 10 wt. % of the surfactant and all ranges and values there between including ranges of 0.5 to 1.0 wt. %, 1.0 to 1.5 wt. %, 1.5 to 2.0 wt. %, 2.0 to 2.5 wt. %, 2.5 to 3.0 wt. %, 3.0 to 3.5 wt. %, 3.5 to 4.0 wt. %, 4.0 to 4.5 wt. %, 4.5 to 5.0 wt. %, 5.0 to 5.5 wt. %, 5.5 to 6.0 wt. %, 6.0 to 6.5 wt. %, 6.5 to 7.0 wt. %, 7.0 to 7.5 wt. %, 7.5 to 8.0 wt. %, 8.0 to 8.5 wt. %, 8.5 to 9.0 wt. %, 9.0 to 9.5 wt. %, and 9.5 to 10.0 wt. %.

In embodiments of the invention, the organic solvent in the cleaning solution includes an alkyl glycol solvent. Non-limiting examples of the alkyl glycol solvent may include butyldiglycol, dipropylene glycol, alkyl ethers of ethylene glycol or propylene glycol, and combinations thereof. According to embodiments of the invention, the alkaline component of the cleaning solution includes sodium hydroxide, potassium hydroxide, or combinations thereof. The surfactant in the cleaning solution may include an alkyl polyglucoside. Non-limiting examples of the alkyl polyglucoside include D-glucopyranose, lauryl glucosides, myristyl glucosides, and combinations thereof. In some aspects, the balance of water in the cleaning solution may include demineralized water, soft water, reverse osmosis water, distilled water, or combinations thereof.

According to embodiments of the invention, as shown in block 102, method 100 may comprise treating the cleaned hard-coated ophthalmic lens with an alkaline solution to produce an alkaline-treated hard-coated ophthalmic lens. In some aspects, the alkaline solution comprises sodium hydroxide, potassium hydroxide, or combinations thereof. The concentration of the alkaline solution may be in a range of 8 to 12 wt. % and all ranges and values there between including ranges of 8 to 8.2 wt. %, 8.2 to 8.4 wt. %, 8.4 to 8.6 wt. %, 8.6 to 8.8 wt. %, 8.8 to 9.0 wt. %, 9.0 to 9.2 wt. %, 9.2 to 9.4 wt. %, 9.4 to 9.6 wt. %, 9.6 to 9.8 wt. %, 9.8 to 10.0 wt. %, 10.0 to 10.2 wt. %, 10.2 to 10.4 wt. %, 10.4 to 10.6 wt. %, 10.6 to 10.8 wt. %, 10.8 to 11.0 wt. %, 11.0 to 11.2 wt. %, 11.2 to 11.4 wt. %, 11.4 to 11.6 wt. %, 11.6 to 11.8 wt. %, and 11.8 to 12.0 wt. %. In some aspects, the treating in block 102 includes submerging the cleaned hard-coated ophthalmic lens in the alkaline solution. The treating at block 102 may further include applying ultrasonic power through the alkaline solution and the cleaned hard-coated ophthalmic lens. In some aspects of the embodiments, the ultrasonic power at block 102 may have a frequency of about 33 MHz at full scale. In some instances, the ultrasonic power at block 102 may have a frequency of about 25% to 45% of the 33 MHz full scale frequency. In some aspects, the temperature during treating at block 102 may be maintained at about 10° C. above the ambient temperature. In some aspects, the temperature of treating at block 102 may be about 60° C. In some aspects, the duration of the treating at block 102 may be in a range of 1 to 8 minute and all ranges and values there between including ranges of 1 to 2 minutes, 2 to 3 minutes, 3 to 4 minutes, 4 to 5 minutes, 5 to 6 minutes, 6 to 7 minutes, and 7 to 8 minutes.

According to embodiments of the invention, method 100 may comprise treating the alkaline-treated hard-coated ophthalmic lens with a stripping solution to strip at least a portion of the hard-coating from the alkaline-treated hard-coated ophthalmic lens to produce a cleaned and stripped ophthalmic lens, as shown in block 103. In some aspects, the cleaned and stripped ophthalmic lens includes substantially no sign of chemical attack and/or substantially no residual hard coating thereon.

In embodiments of the invention, the treating at block 103 may include submerging the alkaline-treated hard coated ophthalmic lens in the stripping solution and agitating the stripping solution. The treating at block 103 may further include applying ultrasonic power to the stripping solution and the alkaline-treated hard-coated ophthalmic lens. In some aspects, the frequency of the ultrasonic power at block 103 may have a frequency of about 33 MHz at full scale. In some instances, the ultrasonic power at block 103 may have a frequency of about 25% to 45% of the 33 MHz full scale frequency. In embodiments of the invention, the temperature at block 103 may be 10° C. above the ambient temperature. In some aspects, the temperature at block 103 may be about 50° C. In some aspects of the embodiments, the duration of the treating at block 103 may be in a range of 1 to 8 minutes and all ranges and values there between including ranges of 1 to 2 minutes, 2 to 3 minutes, 3 to 4 minutes, 4 to 5 minutes, 5 to 6 minutes, 6 to 7 minutes, and 7 to 8 minutes.

In some aspects, the stripping solution may include an organic solvent, an alkaline component, a surfactant, and a balance of water. The stripping solution may be nonflammable. In some aspects, the stripping solution may comprise 10 to 40 wt. % of the organic solvent and all ranges and values there between including ranges of 10 to 12 wt. %, 12 to 14 wt. %, 14 to 16 wt. %, 16 to 18 wt. %, 18 to 20 wt. %, 20 to 22 wt. %, 22 to 24 wt. %, 24 to 26 wt. %, 26 to 28 wt. %, 28 to 30 wt. %, 30 to 32 wt. %, 32 to 34 wt. %, 34 to 36 wt. %, 36 to 38 wt. %, and 38 to 40 wt. %. In some aspects, the stripping solution may comprise 1 to 20 wt. % of the alkaline component and all ranges and values there between including ranges of 1 to 2 wt. %, 2 to 4 wt. %, 4 to 6 wt. %, 6 to 8 wt. %, 8 to 10 wt. %, 10 to 12 wt. %, 12 to 14 wt. %, 14 to 16 wt. %, 16 to 18 wt. %, and 18 to 20 wt. %. In some aspects of the embodiments, the stripping solution comprises 0.5 to 10 wt. % of the surfactant and all ranges and values there between including ranges of 0.5 to 1.0 wt. %, 1.0 to 1.5 wt. %, 1.5 to 2.0 wt. %, 2.0 to 2.5 wt. %, 2.5 to 3.0 wt. %, 3.0 to 3.5 wt. %, 3.5 to 4.0 wt. %, 4.0 to 4.5 wt. %, 4.5 to 5.0 wt. %, 5.0 to 5.5 wt. %, 5.5 to 6.0 wt. %, 6.0 to 6.5 wt. %, 6.5 to 7.0 wt. %, 7.0 to 7.5 wt. %, 7.5 to 8.0 wt. %, 8.0 to 8.5 wt. %, 8.5 to 9.0 wt. %, 9.0 to 9.5 wt. %, and 9.5 to 10.0 wt. %.

In some aspects of the embodiments, the organic solvent in the stripping solution includes an alkyl glycol solvent. Non-limiting examples of the alkyl glycol solvent may include butyldiglycol, dipropylene glycol, alkyl ethers of ethylene glycol or propylene glycol, and combinations thereof. According to embodiments of the invention, the alkaline component of the stripping solution includes sodium hydroxide, potassium hydroxide, or combinations thereof. The surfactant in the stripping solution may include an alkyl polyglucosides. Non-limiting examples of the alkyl polyglucosides include D-glucopyranose, lauryl glucosides, myristyl glucosides, and combinations thereof. In some aspects, the balance of water in the stripping solution may include demineralized water, soft water, reverse osmosis water, distilled water, or combinations thereof.

According to embodiments of the invention, method 100 may include rinsing the ophthalmic lens with water after the treating step of at least one of blocks 101 to 103. In some aspects, the ophthalmic lens may be rinsed after the treating step at each of blocks 101 to 103. In some aspects, the water used for each rinsing step after each of blocks 101 to 103 is independently selected from soft water, demineralized water, deionized water, and combinations thereof. In some aspects, the water used in the rinsing step after each of blocks 101 to 103 is soft water. The rinsing after block 103 may further include rinsing the ophthalmic lens with demi water after rinsing it with soft water.

In some aspects, the rinsing of the ophthalmic lens may be performed at ambient temperature. In some aspects of the embodiments, ultrasonic power is applied to the water and the ophthalmic lens during the rinsing steps. The frequency of the ultrasonic power during the rinsing step may be about 33 MHz at full scale. In some instances, the ultrasonic power in each rinsing step may have a frequency of about 25% to 45% of the 33 MHz full scale frequency. In some aspects, the rinsing duration may be in a range of 1 to 8 minute and all ranges and values there between including ranges of 1 to 2 minutes, 2 to 3 minutes, 3 to 4 minutes, 4 to 5 minutes, 5 to 6 minutes, 6 to 7 minutes, and 7 to 8 minutes.

Embodiments of the invention may include a single-pass cleaning and tripping system for cleaning a hard-coated ophthalmic lens and stripping at least a portion of the ophthalmic lens hard coating. The system may comprise a single apparatus adapted to implement method 100 as shown in FIG. 1. In some aspects, the system may include a chamber for holding one or more ophthalmic lenses. The system may include a liquid application module configured to apply solutions and/or water including the cleaning solution, the stripping solution, and the rinsing water to the hard-coated ophthalmic lens. In some aspects, the system may include an ultrasonic module configured to apply ultrasonic power to the ophthalmic lens, the cleaning solution, the stripping solution, and the rinsing water. In some aspects, the system may further include a temperature module configured to adjust the temperature of the chamber for holding the ophthalmic lenses. The system may include a control module configured to control the treating duration, rinsing duration, the ultrasonic power and frequency, and the temperature in each treating step. In some aspects, the system may include the cleaning solution and the stripping solution used in method 100.

Although embodiments of the present invention have been described with reference to blocks of FIG. 1, it should be appreciated that operation of the present invention is not limited to the particular blocks and/or the particular order of the blocks illustrated in FIG. 1. Accordingly, embodiments of the invention may provide functionality as described herein using various blocks in a sequence different than that of FIG. 1.

As part of the disclosure of the present invention, a specific example is included below. The example is for illustrative purposes only and is not intended to limit the invention. Those of ordinary skill in the art will readily recognize parameters that can be changed or modified to yield essentially the same results.

Example 1

Cleaning and Stripping Hard-Coated Ophthalmic Lenses

Various hard coated lenses including CR-39 (diethylene glycol bis (alyl carbonate)), POLY (poly diphenyl carbonate), Stylis 1.67 (Polythiourethane), and Stylis 1.74 (episulphides based polymer) lenses, were cleaned and the hard coatings were stripped using both a standard method and the process of the present invention. The results of the two methods were compared.

Cleaning and Stripping of Hard-Coated Lenses Using a Standard Method

Each of the $1^{st}$ pass and reworked CR-39, POLY, Stylis 1.67, and Stylis 1.74 lenses was treated sequentially in two apparatuses. In the first apparatus, the lenses were treated sequentially by J2L9 (manufactured by Société Pour le Développement de Technologies Avancées, France) rinse agent at 38° C., 5 wt. % Optical 10 at ambient temperature, 5 wt. % Optical 10L (manufactured by NGL CLEANING TECHNOLOGY SA, Switzerland) at 50° C., 5 wt. % Ceroweg cleaning solution (manufactured by NGL CLEANING TECHNOLOGY SA, Switzerland) at 50° C., 10 wt. % NaOH at 60° C., soft water at ambient temperature, and deionized water at ambient temperature. The lenses obtained after the treatment from the first apparatus were further treated sequentially by Meliack detergent (Manufactured by NAGA, France) at 50° C., soft water at ambient temperature, Meliack at 50° C., soft water at ambient temperature, 10 wt. % NaOH at 60° C., soft water at ambient temperature, deionized water at ambient temperature in the second apparatus. The primary compositions of Meliack, J21-9, and Ceroweg are shown in Tables 1, 2, and 3, respectively. Optical 10L contains a slightly acidic (pH 6.2 at 1%) biodegradable liquid. Ultrasonic was applied to the lenses and solutions/water during the whole treating process. The total treatment time was about 72 minutes. The duration for each treating step was substantially the same. Each of the lenses obtained after the treatment of the second apparatus was evaluated and graded. The results are shown in Tables 4 and 5. The water and electricity consumption of the whole process was further calculated.

TABLE 1

Composition of Meliack detergent

| chemical product | Range of % |
| --- | --- |
| 1-methoxy-2-propanol | 20-50% |
| Nonylphenol ethoxylate | 3-7% |
| Potassium Hydroxide | 3-7% |

TABLE 2

Composition of J2L-9

| chemical product | Range of % |
| --- | --- |
| Anionic surfactants | 3% |
| Ethoxylated alcohol | 45% |
| Inorganic salts (Sodium carbonate) | 1.5% |
| Sodium sulfate | 0.5% |
| Water | 50% |

TABLE 3

Composition of Ceroweg

| chemical product | Range of % |
| --- | --- |
| Sodium hydroxide | 2.5-10% |
| Potassium hydroxide | 10-25% |
| Tetrapotassium pyrophosphate | 2.5-10% |

Cleaning and Stripping of Hard Coated Lenses Using the Single Pass Method of the Present Invention Each of $1^{st}$ pass and reworked CR-39, POLY, Stylis 1.67, and Stylis 1.74 lenses was treated in a single apparatus (the second apparatus). The lenses were treated sequentially by the cleaning solution at 38° C., soft water at ambient temperature, 10 wt. % NaOH at 60° C., soft water at ambient temperature, the stripping solution at 50° C., soft water at ambient temperature, and deionized water. The treatment duration for each of the solutions and/or water was about 4 minutes. The total duration for the whole process was about 32 minutes. The cleaning solution contained 1 to 2 wt. % D-glucopyranose, 2 to 5 wt. % NaOH (99 wt. %), 18 to 25 wt. % butyldiglycol, and demineralized water. The stripping solution contained 2 to 5.5 wt. % D-glucopyranose, 3 to 10 wt. % NaOH (99 wt. %), 20 to 30 wt. % dipropylene glycol, and demineralized water. Ultrasonic power was applied to the lenses during the whole treating process at 25 to 45% of the full scale level of 33 MHz. Agitation of liquid was applied when the lenses were treated with the stripping solution. No agitation was applied to any other solutions/water during the treating steps. Each of the lenses obtained after the whole treatment process was evaluated and graded. The results are shown in Tables 6 and 7. The water and electricity consumption of the whole process was further calculated.

Comparisons of Results Between the Two Methods

As shown in Tables 4 and 6, the method of the present invention showed superior yield on cleaning and stripping hard coatings on POLY, Sylis 1.67, and Sylis 1.74 lenses for the $1^{st}$ pass lenses (lenses that has not had a failed or defected hard coatings thereon). For CR-39 $1^{st}$ pass lenses, the two methods showed comparable yield on cleaning and stripping hard coatings on the lenses. For the second pass (reworked) lenses, as shown in Tables 5 and 7, the method of the present invention showed superior yield and quality for cleaning and stripping Stylis 1.67 and Stylis 1.74 lenses. The term "yield" means the percentage of lenses that is perfectly clean and free of dust or varnish particles after the cleaning and stripping process. For the quality of stripping the hard coating, both methods produced high-quality stripped CR-39 lenses. For $1^{st}$ pass lenses, the method of the present invention produce higher quality POLY and Stylis 1.74 lenses than the standard method. For reworked lenses, the present invention produces higher quality Stylis 1.67 and Stylils 1.74 lenses. However, total operating duration of the method of the present invention was about half of the duration of the standard method. The electricity and water consumption for the method of the present invention was about 50% less than the standard method. Furthermore, the chemical consumption and the low toxicity of the chemicals used in the method of present invention rendered it more environmental friendly than the standard method. Therefore, overall, the method of the present invention is more advantageous than the standard method.

TABLE 4

Results of the cleaning and stripping using a standard method for 1st pass
Standard method-1st pass

| Type of lens | Quality of the cleaning/stripping | Yield |
| --- | --- | --- |
| CR-39 | Good* | ≥95% |
| POLY | Acceptable** | 85-90% |
| Stylis 1.67 | Good* | ≥90% |
| Stylis 1.74 | Acceptable** | 85-90% |

*good indicates substantially none of the lenses showed signs of chemical attack or lacquer residues.
**acceptable indicates that sometimes is required to repeat the cleaning/stripping process.

TABLE 5

Results of the cleaning and stripping using a standard method for reworked lenses
Standard method-reworked lens

| Type of lens | Quality of the cleaning/stripping | Yield |
| --- | --- | --- |
| CR-39 (varnishes RI = 1.5) | Good* | ≥95% |
| POLY (varnishes RI = 1.5) | Good* | ≥95% |
| Stylis 1.67 (varnishes RI = 1.5) | Acceptable** | 85 to 95% |
| Stylis 1.74 (varnishes RI = 1.6) | Poor*** | ≤80% |

*good indicates substantially none of the lenses showed signs of chemical attack or lacquer residues.
**acceptable indicates that sometimes is required to repeat the cleaning/stripping process.
***poor indicates the stripping and cleaning process has to be repeated, sometimes for three times.

TABLE 6

Results of the cleaning and stripping using the method of the present invention for 1st pass
Method of the present invention-1st pass

| Type of lens | Quality of the cleaning/stripping | Yield |
| --- | --- | --- |
| CR-39 | Good* | ≥95% |
| POLY | Good* | ≥95% |
| Stylis 1.67 | Good* | ≥95% |
| Stylis 1.74 | Good* | ≥95% |

*good indicates substantially none of the lenses showed signs of chemical attack or lacquer residues.

TABLE 7

Results of the cleaning and stripping using the method of the present invention for reworked lenses
Method of the present invention-reworked lens

| Type of lens | Quality of the cleaning/stripping | Yield |
| --- | --- | --- |
| CR-39 (varnishes RI = 1.5) | Good* | ≥95% |
| POLY (varnishes RI = 1.5) | Good* | ≥95% |
| Stylis 1.67 (varnishes RI = 1.5) | Good* | ≥95% |
| Stylis 1.74 (varnishes RI = 1.6) | Good* | ≥95% |

*good indicates substantially none of the lenses showed signs of chemical attack or lacquer residues.

The invention claimed is:

1. A single-pass process for cleaning a hard-coated ophthalmic lens and stripping at least a portion of the hard-coated ophthalmic lens, the process comprising the steps of:
   treating by submerging the hard-coated ophthalmic lens with a cleaning solution to produce a cleaned hard-coated ophthalmic lens, said cleaning composition comprising:
   10 wt. % to 40 wt. % of an organic solvent;
   1 wt. % to 20 wt. % of an alkaline component comprising sodium hydroxide and/or potassium hydroxide;
   0.5 wt. % to 3 wt. % of a surfactant comprising alkyl polyglucoside; and
   a balance of water;
   treating by submerging the cleaned hard-coated ophthalmic lens with an alkaline solution to produce an alkaline-treated hard-coated ophthalmic lens; and
   treating by submerging the alkaline-treated hard-coated ophthalmic lens with a stripping solution to strip at least a portion of the hard-coat from the alkaline-treated hard-coated ophthalmic lens to produce a cleaned and stripped ophthalmic lens, said stripping composition comprising:
   10 wt. % to 40 wt. % of an organic solvent;
   1 wt. % to 20 wt. % of an alkaline component which is sodium hydroxide and/or potassium hydroxide;
   0.5 wt. % to 6 wt. % of a surfactant comprising alkyl polyglucoside; and
   a balance of water;
   wherein each of the treating steps is independently performed at a temperature that is at least 10° C. greater than ambient temperature, and wherein ultrasonic power is transmitted to the ophthalmic lens during all of the treating steps with a frequency of about 25% to 45% of a full scale frequency level of 33 Mhz, and a duration of each treating step is in a range of 1 to 8 minutes.

2. The process of claim 1, wherein the cleaning solution comprises:
   10 wt. % to 35 wt. % of an organic solvent;
   1 wt. % to 10 wt. % of an alkaline component;
   0.5 wt. % to 3 wt. % of a surfactant; and
   a balance of water.

3. The process of claim 1, wherein the stripping solution comprises:
   12 wt. % to 30 wt. % of an organic solvent;
   1 wt. % to 7 wt. % of an alkaline component;
   0.5 wt. % to 3 wt. % of a surfactant; and
   a balance of water.

4. The process of claim 1, wherein the organic solvent is butyldiglycol or dipropylene glycol.

5. The process of claim 1, further comprising a step of rinsing the ophthalmic lens with water after each of the treating steps.

6. The process of claim 2, wherein the organic solvent is an alkyl glycol solvent.

7. The process of claim 2, wherein the alkaline component is sodium hydroxide or potassium hydroxide.

8. The process of claim 3, wherein the organic solvent is an alkyl glycol solvent.

9. The process of claim 3, wherein the organic solvent is butyldiglycol or dipropylene glycol.

10. The process of claim 3, wherein the alkaline component is sodium hydroxide or potassium hydroxide.

11. The process of claim 5, wherein the step of rinsing the ophthalmic lens with water after each of the treating steps is performed at ambient temperature.

12. The process of claim 5, wherein ultrasonic power is transmitted to the ophthalmic lens during at least one of the water rinsing steps.

13. The process of claim 11, wherein the water used for the step of rinsing the ophthalmic lens after each of the treating steps is independently selected from soft water, demineralized water, and deionized water.

* * * * *